(12) United States Patent
Beumer et al.

(10) Patent No.: US 7,906,496 B2
(45) Date of Patent: Mar. 15, 2011

(54) CARBOXYLIC ACID DERIVATIVES

(75) Inventors: Raphael Beumer, Lörrach (DE); Jochen Klock, Freiburg (DE); Stefan Martin Stoeckli, Basel (CH)

(73) Assignee: DSM IP Assets B.V., Heerlen (NL)

( * ) Notice: Subject to any disclaimer, the term of this patent is extended or adjusted under 35 U.S.C. 154(b) by 287 days.

(21) Appl. No.: 11/990,217

(22) PCT Filed: Sep. 14, 2006

(86) PCT No.: PCT/EP2006/008965
§ 371 (c)(1),
(2), (4) Date: Feb. 8, 2008

(87) PCT Pub. No.: WO2007/039059
PCT Pub. Date: Apr. 12, 2007

(65) Prior Publication Data
US 2009/0258887 A1    Oct. 15, 2009

(30) Foreign Application Priority Data
Sep. 20, 2005    (EP) .................................... 05020446

(51) Int. Cl.
C07D 211/72    (2006.01)
C07D 211/84    (2006.01)
C07D 213/56    (2006.01)

(52) U.S. Cl. ....................................... 514/167; 546/316
(58) Field of Classification Search .................. 514/167; 546/316
See application file for complete search history.

(56) References Cited

U.S. PATENT DOCUMENTS

| 4,925,929 | A | | 5/1990 | Toda et al. |
| 5,002,935 | A | * | 3/1991 | Bodor .............................. 514/58 |
| 2003/0175234 | A1 | | 9/2003 | Hernandez et al. |

FOREIGN PATENT DOCUMENTS

| EP | 1 514 536 | 3/2005 |
| GB | 826 790 | 1/1960 |
| WO | 96/03411 | 2/1996 |
| WO | 00/62741 | 10/2000 |

OTHER PUBLICATIONS

Goodman and Gilman's (The Pharmacological Basis of Therapeutics (Tenth Edition (2001), McGraw Hill, Chapter I, pp. 3-29).*
Naldi et al. (Expert Opinion on Emerging Drugs (2009) 14:145-163).*
Plotz et al. (Expert Opinion on Emerging Drugs (2010) 15:249-267).*
Tatlock et al., "Structure based Design of Novel Clacineurin (PP2B) Inhibitors", *Bioorganic and Medicinal Chemistry Letters*, vol. 7, No. 8, 1997, pp. 1008-1012, XP002411032.
Fairlamb et al., "Identification of Novel Mammalian Squalene Synthase Inhibitors Using a Three-Dimensional Pharmacophore" *Bioorganic and Medicinal Chemistry*, vol. 10, 2002, pp. 2641-2656, XP002411033.
Sharma et al., "A Mild and Highly Selective Deprotective Method of Prenyl Ethers Using Ytterbium Triflate", *Journal of Organic Chemistry*, vol. 63, 1998, pp. 9103-9104, XP002411034.
Database WPI Week 198511, Derwent Publications Ltd., London, GB; AN 1985-064790, XP002411612.
International Search Report for PCT/EP2006/008965 mailed Dec. 19, 2006.
Written Opinion for PCT/EP2006/008965 mailed Dec. 19, 2006.

* cited by examiner

*Primary Examiner* — Brandon J Fetterolf
*Assistant Examiner* — Marcos Sznaidman
(74) *Attorney, Agent, or Firm* — Nixon & Vanderhye P.C.

(57) ABSTRACT

The present invention is concerned with novel arylalkyl carboxylic acid derivatives, more specifically, with acylates of arylalkyl carboxylic acids with naturally occurring, non-toxic hydroxy, sulfhydryl, amino or imino compounds, and to compositions containing them. The compositions are preferably cosmetic preparations.

4 Claims, No Drawings

CARBOXYLIC ACID DERIVATIVES

This application is the U.S. national phase of International Application No. PCT/EP2006/008965 filed 14 Sep. 2006 which designated the U.S. and claims priority to European Patent Application No. 05020446.0 filed 20 Sep. 2005, the entire contents of each of which are hereby incorporated by reference.

The present invention is concerned with novel arylalkyl carboxylic acid derivatives, more specifically, with acylates of arylalkyl carboxylic acids with naturally occurring, non-toxic hydroxy, sulfhydryl, amino or imino compounds, and to compositions containing them. The compositions are preferably cosmetic preparations.

More particularly, the invention is concerned with compounds of the general formula

$$[\text{Ph-}(CH_2)_n\text{—CO}]_m\text{—X} \qquad (I)$$

wherein Ph is phenyl or substituted phenyl, n is 1 or 3, m is an integer of at least 1, and X is a moiety from a naturally occurring, non-toxic compound carrying at least one hydroxyl, sulfhydryl, amino or imino group which moiety is formed by removal of a hydrogen atom from said hydroxyl, sulfhydryl, amino or imino group; except that X is not an amino acid or peptide comprising up to 6 amino acids.

The term 'naturally occurring, non-toxic hydroxyl, sulfhydryl, amino or imino compounds' comprises natural occurring compounds such as vitamins, terpenes, chromanes, flavones, catechols, pyrimidines as well as synthetic derivatives or analogues thereof which have been modified in order to make them susceptible for an attachment to the $[\text{Ph-}(CH_2)_n\text{—CO}]_m$ moiety.

It has been found that the compounds provided by the present invention are particularly useful for treating wrinkles but also for thickening the epidermis, repairing the skins lipid barrier, for protection against hair loss and for improving hair growth.

Human skin undergoes certain normal cornification processes which give the skin its characteristic appearance. Casual factors or external factors such as a raw climate, wind, photo-damage and irritation triggered by the sun, rain and snow, however, disturb this normal condition of the skin, and there appears a roughness, a formation of scales (for example on the scalp), an excessive keratinization and similar phenomena. Furthermore, in the course of aging of the skin various signs appear that are especially reflected by a change in the structure and function of the skin. One of these signs is the appearance of fine lines and deep wrinkles, the size and number of which increases with age. The micro relief of the skin becomes less uniform and is of anisotropic nature. In parallel with age the skin becomes more sensitive towards disturbing influences, either intrinsic or extrinsic, which may result in itch, redness or even darker spots, particular on hands and the facial area due to pigmentation disorders. These unwanted signs may lead to an undesired age judgment of a person.

Cosmetic preparations are essentially useful for skin care. One aim of skin care in the cosmetic sense is to strengthen or rebuild the skin's natural function as a barrier against environmental influences (e.g. UV-light, dirt, chemicals, micro-organisms) and against the loss of endogenous substances (e.g. water, natural lipids, electrolytes). If this function becomes impaired, increased resorption of toxic or allergenic substances or attack by microorganisms may result, leading to toxic or allergic skin reactions.

Another aim of skin care is to compensate for the loss by the skin of lipids and water caused by daily washing. This is particularly important, if the natural regeneration ability is inadequate. Furthermore, skin care products should protect against environmental influences, in particular against sun and wind, and delay skin aging.

Strengthening or thickening of the epidermis together with an optimized skin barrier lipid synthesis can rebuild the skin's barrier ability and is therefore of significant cosmetic value. Reduced transepidermal water loss (TEWL) is a sign of an intact lipid barrier, which acts also as first defense line to protect against the appearance of skin wrinkles.

Another strategy to fight wrinkles is to stimulate the collagen synthesis in the dermis. A number of degenerative processes act on the collagen matrix and is triggered by extrinsic factors like UV radiation, pollution in general and particular cigarette smoke or intrinsic factors leading to any chronic or sub chronic inflammation. Destruction and/or impaired repair efficacy leads to a denser and less elastic macro structure of the dermis, which in turn leads to the formation of deep wrinkles. Enhancing the de novo synthesis of collagen or other structural proteins of the dermis is considered a valuable therapy to reduce the existing wrinkles and to protect against the appearance of new wrinkles.

Of particular importance for anti-aging cosmetics is to inhibit the senescence of skin cells in order to keep their regular metabolic level on a constant and beneficial level.

Hair loss or alopecia is a common affliction of humans. The most common form of hair loss in both males and females is patterned baldness or androgenic alopecia.

Hair follicles range in size from small, superficial, vellus follicles to large, deep, terminal follicles. The cyclic growth phases of hair follicles are telogen (resting), anagen I-III (developing), anagen IV-VI (growing) and catagen (involuting).

In the development of androgenic alopecia there is the gradual diminution of follicle size, with conversion of large, terminal follicles, producing thick, pigmented hair fibers (terminal hair) to small vellus follicles producing fine, non-pigmented hair fibers (vellus hair). In addition, the proportion of growing anagen follicles declines.

There exists a wide variety of literature regarding cosmetic preparations, in particular regarding cosmetic preparations for treating wrinkles and for promoting hair growth. As examples of the extensive literature it can be referred e.g. to GB 906,000, EP-A 699 429 or WO 03/086342.

While a variety of technologies exist to prevent and to fight the signs of skin aging, to improve the appearance of the skin or to treat or prevent hair loss, there is still a demand for more efficacious ingredients.

The problem to be solved by the present invention is the provision of novel compounds, of compositions containing these novel compounds, in particular of cosmetic preparations which are particularly useful for treating and/or preventing wrinkles, thickening of the epidermis, and preventing and/or treating of hair loss, but also preparations which are useful against other conditions which are observed with skin aging due to environmental or other external influences or due to age. The new compounds should have an activity which is comparable to the activity of known cosmetically active compounds but preferably is better than the activity of the prior art compounds.

This problem is solved on the basis of the unexpected finding that certain arylalkyl carboxylic acylates with naturally occurring, non-toxic hydroxyl, sulfhydryl, amino or imino compounds show activity in cosmetic applications and related pharmaceutical applications, in particular for treating and preventing wrinkles and hair loss and thickening the epidermis, but also for ameliorating the effects of aging of the skin, which may be caused by external or environmental hazards or by the natural aging of the skin.

Accordingly, in one aspect, the present invention is concerned with compounds represented by general formula (I) as shown above. In another aspect, the invention is concerned with compositions, particularly cosmetic preparations comprising a compound of the formula (I). In still another aspect, the invention is concerned with the use of the compounds of formula (I) for treating and preventing wrinkles and hair loss and thickening the epidermis, but also for ameliorating the effects of aging of the skin, which may be caused by external or environmental hazards or by the natural aging of the skin, and with a method of treating and preventing the aforesaid conditions by administering an effective amount of a topical composition comprising a compound of formula (I) on the appropriate portions of the skin of an individual in need of such treatment.

In another embodiment, the invention relates to a method of treatment or prophylaxis of wrinkles or dry skin or sensitive skin or any symptoms caused by negative developments of the physiological homeostasis of healthy skin, promotion of hair growth, protection from hair loss, a thickening of the epidermis, anti-acne, the inhibition of senescence of skin cells, prevention or treatment of photo damage, prevention or treatment of oxidative stress phenomena, prevention or treatment of cellulite, prevention or treatment of pigmentation disorders and/or even the skin tone, prevention and treatment of disturbances in ceramide and lipid synthesis, prevention of excess sebum production, reduction of activities of matrix metallo proteases or other proteases in the skin, treatment and prevention of inflammatory skin conditions including atopic eczema, polymorphic light eruption, psoriasis, vertiligo, prevention and treatment of itchy or irritated skin, which comprises applying an effective amount of composition comprising a compound of formula (I) on the appropriate portions of the skin of the individual in need of such treatment.

The term 'an effective amount' refers to an amount necessary to obtain a physiological effect. The physiological effect may be achieved by one single application or by repeated applications. The dosage applied may, of course, vary depending upon known factors, such as the physiological characteristics of the particular composition and its mode and route of administration; the age, health and weight of the recipient; the nature and extent of the symptoms; the kind of concurrent treatment; the frequency of treatment; the concentration of the compound of formula (I) in the topical composition; and the effect desired and can be adjusted by a person skilled in the art.

The amount of the topical composition which is to be applied to the skin depends on the concentration of the active ingredients, i.e. the compound of formula (I), in the compositions and the desired cosmetic or pharmaceutical effect. For example, application can be such that a crème is applied to the skin. A crème is usually applied in an amount of 2 mg crème/cm$^2$ skin. The amount of the composition which is applied to the skin is, however, not critical, and if with a certain amount of applied composition the desired effect cannot be achieved, a higher concentration of the active ingredients can be used e.g. by applying more of the composition or by applying compositions which contain more active ingredient.

A preferred group of compounds within the scope of formula (I) are those wherein Ph is unsubstituted phenyl. If Ph is substituted phenyl, the phenyl ring may be substituted by up to three substituents which are selected, independently, from hydroxyl, $C_1$-$C_6$ alkyl, $C_2$-$C_6$ alkenyl, $C_1$-$C_6$ alkoxy and $C_2$-$C_6$ alkenyloxy. Preferred substituted phenyl moieties are phenyl mono-substituted by $C_{1-6}$-alkoxy, especially methoxyphenyl.

In all embodiments of the invention compounds within the scope of formula (I) wherein m is 1 are preferred. Most preferred according to the invention are compounds within the scope of formula (I) wherein the residue [Ph-$(CH_2)_n$—CO]$_m$ is derived from phenyl butyric acid and m is 1.

The naturally occurring, non-toxic compound carrying at least one hydroxyl, sulfhydryl, amino or imino group from which the moiety X in formula (I) is derived may be any such compound that can be used in cosmetic applications. Examples of such compounds are fat-soluble vitamin derivatives and analogues thereof, water-soluble vitamins, derivatives or analogues thereof, carbohydrates, α-hydroxy-carboxylic acids, aliphatic alcohols and polyols, amino alcohols, chromanes and flavones, derivatives and analogues thereof, pyrimidines or purines or analogues thereof, terpenes, and catechols; particular examples being (CAS numbers given in parenthesis) glucoses with open or ring form (50-99-7), Tocopherols like DL-α-tocopherol (10191-41-0), Panthenol (81-13-0), Pantothenic acid (79-83-4), Pyridoxines such as vitamin $B_6$ (65-23-6), Kinetin (525-79-1), Vanillin (121-33-5), Fenchol (1632-73-1), Quercetin (117-39-5), Wogonin (632-85-9), Delphinidin (528-53-0), Silymarin (65666-07-1), Gossypin (652-78-8), Equol (531-95-3), Shikimic Acid (138-59-0), Gramin (87-52-5), Carnitin (461-06-3), Glutathion (70-18-8), Ginkgetin (481-46-9), Insulin (11061-68-0), Farnesol (106-28-5), Thiamine (67-03-8), Riboflavin (83-88-5), Bisabolol (23089-26-1), Ascorbic Acid (50-81-7), Stay-C 50 (66170-10-3), Folic Acid (59-30-3), Daidzein (486-66-8), Genistein (446-72-0), Resveratrol (501-36-0), Betanin (7659-95-2), Phytantriol (74563-64-7), Retinol (68-26-8), Vitamin D3 (67-97-0), Hy-D (63283-36-3), Astaxanthin (754245-2), Lutein (127-40-2), Zeaxanthin (144-68-3), alpha-hydroxy phytanic acid (14721-68-7), beta-Sitosterol (64997-52-0), Menthol (89-78-1), Allantoin (97-59-6), epigallocatechin gallate (EGCG) (989-51-5), Glycerol (56-81-5), Phytol (150-86-7), lactic acid (50-21-5), Biotin (58-85-5), phytanic acid (14721-66-5) and tetradecylthioacetic acid (2921-20-2).

Preferably, the naturally occurring, non-toxic compound carrying at least one hydroxyl, sulfhydryl, amino or imino group from which the moiety X in formula (I) is derived is a fat-soluble vitamin or derivative or analogue, in particular a tocopherol, a carotenoid and vitamin D3 or a hydroxyl derivative thereof;

a water-soluble vitamin, derivatives or analogues thereof belonging to the vitamin B or vitamin C group, in particular panthenol, pantothenic acid, pyridoxines, thiamine, riboflavin, nicotinamide, 2-hydroxyethylnicotinamide, folic acid, ascorbic acid or ascorbic acid phosphate, more in particular nicotinamide, 2-hydroxyethylnicotinamide, panthenol, ascorbic acid or ascorbic acid phosphate;

a chromane, flavone, derivatives and analogues thereof, in particular equol, quercetin, delphinidine, silymarin, daidzein, or genistein;

a pyrimidine or purine or analogue thereof, in particular kinetin or allantoin;

a terpene preferably farnesol, bisabolol, phytol and menthol, in particular bisabolol; or a catechol, in particular epigallocatechingallate.

Of particular interest as compounds from which the moiety X is derived, i.e. compounds of the formula XH, are panthenol, bisabolol, kinetin and 2-hydroxyethylnicotinamide.

Further examples of compounds of formula (I) are the phenyl butyric acid ester of nicotinic acid 2-hydroxyethylamide, glycerol-1-phenylbutyrate-3-nicotinate and the phenyl acetic acid ester of phytanic acid 2-hydroxyethylamide.

Especially preferred according to the invention are the following compounds of formula (I):
4-phenylbutyric acid 2-[(pyridine-3-carbonyl)amino]-ethyl ester 4-phenylbutyric acid 3-(2,4-dihydroxy-3,3-dimethyl-butyrylamino)-propyl ester.
N-furan-2-yl-methyl-4-phenyl-N-(9H-purin-6-yl)-butyramide 4-phenylbutyric acid 1,5-dimethyl-1-(4-methyl-cyclohex-3-enyl)-hex-4-enyl ester.

In accordance of the present invention, the compounds of formula (I) can be prepared in a manner known per se, e.g. as disclosed in the Examples or in analogy thereto. Generally, the compounds of formula (I) can be prepared by acylating a compound of the formula XH, wherein X is as defined above, with a compound of the formula Ph-$(CH_2)_n$—COOH or a reactive derivative thereof.

The acylation of the present invention can be carried out in a manner known per se. Suitably, the acylation is carried out using a reactive derivate such as a halogenide, e.g. the chloride or bromide, in the presence of an organic base, e.g. pyridine or an aliphatic amine such as triethylamine, or an inorganic base such as sodium hydride or an alkali carbonate. If required, any groups reactive to the acylating agent which are not intended to be acylated have to be protected. Therefore the acylation of polyfunctional molecules requires versatile protecting groups that can be easily introduced which are orthogonally stable to each other and can be selectively removed under mild conditions. A good selection of the most useful protecting groups for functional and potentially reactive groups which can be easily applied for the above mentioned purpose by people skilled in the art can be found e.g. in P. J. Kocienski, Protecting Groups, 2000, Corrected Edition, Georg Thieme Verlag, Stuttgart, N.Y. and T. W. Greene, P. G. M. Wuts, Protective Groups in Organic Synthesis, $3^{rd}$ Edition, 1999, John Wiley & Sons, Inc., New York.

For instance, when acylating panthenol, the primary and secondary hydroxy groups located in the carboxylic acid portion of the molecule may be protected by forming an acetonide, thus allowing a selective acylation of the hydroxy group located in the amide portion of the molecule. On the other hand, the acylation of compounds of the formula XH which carry more than one reactive OH, SH, amino or imino group may be carried out without intermediary protection of individual reactive groups, thus leading to compounds of the formula (I) wherein m is an integer of greater than 1 with m corresponding to the number of reactive OH, SH, amino or imino groups in the starting compound of formula XH.

For the purposes of the present invention, the compounds of formula (I) can be used alone or in mixtures.

The present invention also provides compositions, in particular topical compositions comprising at least one compound represented by general formula (I), and a cosmetically acceptable excipient or diluent.

In case that the compounds of formula I bear one or more chiral centers the compounds represented by general formula (I) may be present in a racemic mixture, in a mixture of diastereomers or in excess of an enantiomer and/or diastereomer. If one or more chiral centers are present the optical purity of the mixture is preferably ≧80% ee, more preferably ≧90% ee, most preferably ≧95% de. If two or more chiral centers are present the purity of the mixture is preferably ≧80% de, more preferably ≧90% de, most preferably ≧95% de.

The compositions of the present invention are pharmaceutical or cosmetic compositions, preferably cosmetic compositions or cosmetic preparations.

The term "cosmetic preparation" or "cosmetic composition" as used in the present application refers to cosmetic compositions as defined under the heading "Kosmetika" in Römpp Lexikon Chemie, 10th edition 1997, Georg Thieme Verlag Stuttgart, New York.

The compositions of the present invention contain the compound represented by general formula (I) with cosmetically acceptable excipients or diluents. If nothing else is stated, the excipients, additives, diluents, etc. mentioned in the following are suitable for cosmetic compositions.

If nothing else is stated, in this application parts and percentages are per weight and are based on the weight of the composition.

Preferably, the cosmetic or pharmaceutical compositions of the present invention are topical compositions in the form of a suspension or dispersion in solvents or fatty substances, or alternatively in the form of an emulsion or micro emulsion (in particular of O/W or W/O type, O/W/O or W/O/W-type), PET-emulsions, multiple emulsions, bickering emulsions, hydrogels, alcoholic gels, lipogels, one or multiphase solutions or a vesicular dispersion and other usual compositions, which can also be applied by pens, as masks or as sprays. The emulsions can also contain anionic, nonionic, cationic or amphoteric surfactant(s).

Preferred compositions according to the invention are skin care preparations, hair-care preparations, decorative preparations, light protection preparations and functional preparations.

Examples of skin care preparations are, in particular, body oils, body lotions, body gels, treatment creams, skin protection ointments, shaving preparations, such as shaving foams or gels, skin powders such as baby powder, moisturizing gels, moisturizing sprays, revitalizing body sprays, cellulite gels, anti acne preparations and peeling preparations.

Examples of hair care preparations are, for example, hair-washing preparations in the form of shampoos, hair conditioners, hair-care preparations, e.g. treatment preparations, pre-treatment preparations, hair tonics, styling creams, styling gels, pomades, hair rinses, treatment packs, intensive hair treatments, hair-straightening preparations, liquid hair-setting preparations, hair foams and hairsprays and lacquers, perming agents, hair gels, hair fixatives and hair dying or bleaching agents.

Examples of decorative preparations are in particular lipstick, eye shadow, mascaras, dry and moist make-up, rouge, powders, and suntan lotions.

Examples of functional preparations are cosmetic or pharmaceutical compositions containing active ingredients such as hormone preparations, vitamin preparations, vegetable extract preparations, anti-ageing preparations, and antimicrobial (antibacterial or antifungal) preparations without being limited thereto.

Cosmetic compositions in accordance with the invention can be in the form of a liquid, lotion, a thickened lotion, a gel, a cream, a milk, an ointment, a paste, a powder, a make-up, or a solid tube stick and can be optionally be packaged as an aerosol and can be provided in the form of a mousse such as a aerosol mousse, a foam or a spray foams, sprays, sticks, a gel, a plaster, a powder, a cleanser, a soap or aerosols or wipes.

The compositions of the invention can also contain usual cosmetic adjuvants and additives, such as preservatives/antioxidants, fatty substances/oils, water, organic solvents, silicones, thickeners, softeners, emulsifiers, sunscreens, cosmetic actives antifoaming agents, moisturizers, fragrances, surfactants, fillers, sequestering agents, anionic, cationic, nonionic or amphoteric polymers or mixtures thereof, propellants, acidifying or basifying agents, dyes, colorants, pigments or nanopigments, e.g. those suited for providing a photoprotective effect by physically blocking out ultraviolet radiation, or any other ingredients usually formulated into cosmetics. A good overview of suitable additives for cosmetic compositions can also be found e.g. in WO 03/082232. The additives disclosed in this document, in particular the waxes, thickeners, structuring agents, film forming agents and conditioning ingredients are also suitable for the compositions of the present invention and included herein by reference. Of course, the stabilizing compositions disclosed in this document can also be used for preparing the compositions of the present invention.

The composition of the present invention can also contain one or more additional pharmaceutically or cosmetically active ingredients, in particular for preventing or reducing acne, wrinkles, lines, pigmentation, atrophy, inflammation, as well as topical anesthetics, artificial tanning agents and accelerators, antimicrobial agents, and antifungal agents and sun screening additives without being limited thereto.

Examples of such ingredients are peptides (e.g., Matrixyl™ [pentapeptide derivative]), oligopeptides, wax-based synthetic peptides (e.g., octyl palmitate and tribehenin and sorbitan isostearate and palmitoyl-oligopeptide), glycerol, urea, guanidine (e.g. amino guanidine); vitamins and derivatives thereof such as vitamin C (ascorbic acid), vitamin A (e.g., retinoid derivatives such as retinyl palmitate or retinyl propionate), vitamin E (e.g., tocopherol acetate), vitamin $B_3$ (e.g. nicotinamide) and vitamin $B_5$ (e.g. panthenol), vitamin $B_6$ and vitamin $B_{12}$, biotin, folic acid; anti-acne actives or medicaments (e.g. resorcinol, salicylic acid, and the like); antioxidants (e.g. phytosterols, lipoic acid); flavonoids (e.g. isoflavones, phytoestrogens); skin soothing and healing agents such as aloe vera extract, allantoin and the like; agents suitable for aesthetic purposes such as essential oils, fragrances, skin sensates, opacifiers, aromatic compounds (e.g., clove oil, menthol, camphor, eucalyptus oil, and eugenol), desquamatory actives, hydroxy acids such as AHA acids, radical scavengers, farnesol, antifungal actives in particular bisabolol, alkyldiols such as 1,2-pentanediol, hexanediol or 1,2-octanediol, phytol, polyols such as phytanetriol, ceramides and pseudoceramides, amino acids, protein hydrolysates, polyunsaturated fatty acids, plant extracts like kinetin, DNA or RNA and their fragmentation products, carbohydrates, conjugated fatty acids, carnitin, carnosine, biochinonen, phytofluen, phytoen, and their corresponding derivatives.

Additionally the cosmetic and pharmaceutical topical composition of the present invention may contain UV-screening agents (UV-filter). The additional UV-screening agents are advantageously selected from IR, UV-A, UV-B, UV-C and/or broadband filters. Examples of UV-B or broad spectrum screening agents, i.e. substances having absorption maximums between about 290 nm and 340 nm may be organic or inorganic compounds. Organic UV-B or broadband screening agents are e.g. acrylates such as 2-ethylhexyl 2-cyano-3,3-diphenylacrylate (octocrylene, PARSOL® 340), ethyl 2-cyano-3,3-diphenylacrylate and the like; camphor derivatives such as 4-methyl benzylidene camphor (PARSOL® 5000), 3-benzylidene camphor, camphor benzalkonium methosulfate, polyacrylamidomethyl benzylidene camphor, sulfo benzylidene camphor, sulphomethyl benzylidene camphor, therephthalidene dicamphor sulfonic acid and the like; Cinnamate derivatives such as ethylhexyl methoxycinnamate (PARSOL® MCX), ethoxyethyl methoxycinnamate, diethanolamine methoxycinnamate (PARSOL® Hydro), isoamyl methoxycinnamate and the like as well as cinnamic acid derivatives bond to siloxanes; p-aminobenzoic acid derivatives, such as p-aminobenzoic acid, 2-ethylhexyl p-dimethylaminobenzoate, N-oxypropylenated ethyl p-aminobenzoate, glyceryl p-aminobenzoate; benzophenones such as benzophenone-3, benzophenone-4,2,2',4,4'-tetrahydroxybenzophenone, 2,2'-dihydroxy-4,4'-dimethoxybenzophenone and the like; esters of benzalmalonic acid such as di-(2-ethylhexyl) 4-methoxybenzalmalonate; esters of 2-(4-ethoxy-anilinomethylene)propandioic acid such as 2-(4-ethoxy anilinomethylene) propandioic acid diethyl ester as described in the European Patent Publication EP 0895 776; organosiloxane compounds containing benzmalonate groups as described in the European Patent Publications EP 0358584 B1, EP 0538431 B1 and EP 0709080 A1 such as PARSOL® SLX; drometrizole trisiloxane (Mexoryl XL); imidazole derivatives such as e.g. 2-phenyl benzimidazole sulfonic acid and its salts (PARSOL®HS). Salts of 2-phenyl benzimidazole sulfonic acid are e.g. alkali salts such as sodium- or potassium salts, ammonium salts, morpholine salts, salts of primary, sec. and tert. amines like monoethanolamine salts, diethanolamine salts and the like; salicylate derivatives such as isopropylbenzyl salicylate, benzyl salicylate, butyl salicylate, ethylhexyl salicylate (PARSOL® EHS, Neo Heliopan OS), isooctyl salicylate or homomethyl salicylate (homosalate, PARSOL® HMS, Neo Heliopan HMS) and the like; triazine derivatives such as ethylhexyl triazone (Uvinul T-150), diethylhexyl butamido triazone (Uvasorb HEB) and the like. Encapsulated UV-filters such as encapsulated ethylhexyl methoxycinnamate (Eusolex UV-pearls) or microcapsules loaded with UV-filters as e.g. disclosed in EP 1471995 and the like;

Examples of broad spectrum or UV A screening agents i.e. substances having absorption maximums between about 320 nm and 400 nm may be organic or inorganic compounds. Organic broad spectrum or UV A screening agents include e.g. dibenzoylmethane derivatives such as 4-tert.-butyl-4'-methoxydibenzoyl-methane (PARSOL® 1789), dimethoxydibenzoylmethane, isopropyldibenzoylmethane and the like; benzotriazole derivatives such as 2,2'-methylene-bis-(6-(2H-benzotriazole-2-yl)-4-(1,1,3,3-tetramethylbutyl)-phenol (Tinosorb M) and the like; bis-ethylhexyloxyphenol methoxyphenyl triazine (Tinosorb S) and the like; phenylene-1,4-bis-benzimidazolsulfonic acids or salts such as 2,2-(1,4-phenylene)bis-(1H-benzimidazol-4,6-disulfonic acid) (Neoheliopan AP); amino substituted hydroxybenzophenones such as 2-(4-Diethylamino-2-hydroxy-benzoyl)-benzoic acid hexylester (Uvinul A plus) as described in the European Patent Publication EP 1046391; Ionic UV-A filters as described in the International Patent Publication WO2005080341 A1; As dibenzoylmethane derivatives have limited photostability it may be desirable to photostabilize these UV-A screening agents. Thus, the term "conventional UV-A screening agent" also refers to dibenzoylmethane derivatives such as e.g. PARSOL® 1789 stabilized by, e.g. 3,3-Diphenylacrylate derivatives as described in the European Patent Publications EP 0 514 491 B1 and EP 0 780 119 A1; Benzylidene camphor derivatives as described in the U.S. Pat. No. 5,605,680; Organosiloxanes containing benzmalonate groups as described in the European Patent Publications EP 0358584 B1, EP 0538431 B1 and EP 0709080 A1.

A good overview of UV-A- and UV-B screening agents which can be added to the compositions of the present invention can also be found in DE-A 103 27 432. All UV-screening agents disclosed in this document are also useful as components for the compositions of the present invention and are included herein by reference.

A safe and effective amount of the UV-screening agent is used, typically from about 1 wt.-% to about 20 wt.-%, more typically from about 2 wt.-% to about 10 wt.-%.

Other suitable UV-screening agents which may be incorporated into the cosmetic or pharmaceutical topical compositions of the present invention are inorganic pigments such as microparticulated metal oxides (e.g. PARSOL® TX). Examples of such compounds include e.g. titanium dioxide having an average primary particle size of from about 15 nm to about 100 nm, zinc oxide having an average primary particle size of from about 15 nm to about 150 nm, zirconium oxide having an average primary particle size of from about 15 nm to about 150 nm, iron oxide having an average primary particle size of from about 15 nm to about 500 nm, and mixtures thereof. The metal oxide particles may also be coated by metal oxides such as e.g. aluminum or zirconium oxides or by organic coatings such as e.g. polyols, methicone, aluminum stearate, alkyl silane. Such coatings are well known in the art. When used herein, the inorganic sunscreens are present in the amount of from about 0.1 wt.-% to about 20 wt.-%, preferably from about 0.5 wt.-% to about 10 wt.-%, more preferably from about 1 wt.-% to about 5 wt.-%.

The compositions of the present invention preferably contain one or more antioxidants/preservatives. Based on the invention all known antioxidants usually formulated into cosmetics can be used. Especially preferred are antioxidants chosen from the group consisting of amino acids (e.g. glycine, histidine, tyrosine, tryptophan) and their derivatives, imidazole (e.g. urocanic acid) and derivatives, peptides such as D,L-carnosine, D-carnosine, L-carnosine and derivatives (e.g. anserine), carotenoids, carotenes (e.g. α-carotene, β-carotene, lycopene) and derivatives, chlorogenic acid and derivatives, lipoic acid and derivatives (e.g. dihydrolipoic acid), aurothioglucose, propylthiouracil and other thiols (e.g. thioredoxine, glutathione, cysteine, cystine, cystamine and its glycosyl-, N-acetyl-, methyl-, ethyl-, propyl-, amyl-, butyl- and lauryl-, palmitoyl-; oleyl-, γ-linoleyl-, cholesteryl- and glycerylester) and the salts thereof, dilaurylthiodipropionate, distearylthiodipropionate, thiodipropionic acid and its derivatives (ester, ether, peptides, lipids, nucleotides, nucleosides and salts) as well as sulfoximine compounds (such as buthioninsulfoximine, homocysteinsulfoximine, buthioninsulfone, penta-, hexa-, heptathioninsulfoximine) in very low compatible doses (e.g. pmol to μmol/kg), additionally (metal)-chelators (such as α-hydroxyfatty acids, palmic-, phytinic acid, lactoferrin), α-hydroxyacids (such as citric acid, lactic acid, malic acid), huminic acid, gallic acid, gallic extracts, bilirubin, biliverdin, EDTA, EGTA and its derivatives, unsaturated fatty acids and their derivatives (such as γ-linoleic acid, linolic acid, oleic acid), folic acid and its derivatives, ubiquinone and ubiquinol and their derivatives, vitamin C and derivatives (such as ascorbylpalmitate and ascorbyltetraisopalmitate, Mg-ascorbylphosphate, Na-ascorbylphosphate, ascorbylacetate, ascorbylglucoside), tocopherol and derivates (such as vitamin-E-acetate), mixtures of nat. vitamin E, vitamin A and derivatives (vitamin-A-palmitate and -acetate) as well as coniferylbenzoate, rutinic acid and derivatives, α-glycosylrutin, ferulic acid, furfurylidenglucitol, carnosin, butylhydroxytoluene, butylhydroxyanisole, trihydroxybutyrophenone, urea and its derivatives, mannose and derivatives, zinc and derivatives (e.g. ZnO, $ZnSO_4$), selenium and derivatives (e.g. selenomethionine), stilbenes and derivatives (such as stilbenoxide, trans-stilbenoxide) and suitable derivatives (salts, esters, ethers, sugars, nucleotides, nucleosides, peptides and lipids) of the named active ingredients. One or more preservatives/antioxidants may be present in an amount about 0.01 wt. % to about 10 wt. % of the total weight of the composition of the present invention. Preferably, one or more preservatives/antioxidants are present in an amount about 0.1 wt. % to about 1 wt. %.

Typically topical compositions also contain surface active ingredients like emulsifiers, solubilizers and the like. An emulsifier enables two or more not miscible components to be combined homogeneously. Moreover, the emulsifier acts to stabilize the composition. Emulsifiers that may be used in the present invention in order to form O/W, W/O, O/W/O or W/O/W emulsions/microemulsions include sorbitan oleate, sorbitan sesquioleate, sorbitan isostearate, sorbitan trioleate, polyglyceryl-3-diisostearate, polyglycerol esters of oleic/isostearic acid, polyglyceryl-6 hexaricinolate, polyglyceryl-4-oleate, polyglyceryl-4 oleate/PEG-8 propylene glycol cocoate, oleamide DEA, TEA myristate, TEA stearate, magnesium stearate, sodium stearate, potassium laurate, potassium ricinoleate, sodium cocoate, sodium tallowate, potassium castorate, sodium oleate, and mixtures thereof. Further suitable emulsifiers are phosphate esters and the salts thereof such as cetyl phosphate (Amphisol® A), diethanolamine cetyl phosphate (Amphisol®), potassium cetyl phosphate (Amphisol® K), sodium glyceryl oleate phosphate, hydrogenated vegetable glycerides phosphate and mixtures thereof. Furthermore, one or more synthetic polymers may be used as an emulsifier. For example, PVP eicosene copolymer, acrylates/$C_{10-30}$ alkyl acrylate crosspolymer, acrylates/steareth-20 methacrylate copolymer, PEG-22/dodecyl glycol copolymer, PEG-45/dodecyl glycol copolymer, and mixtures thereof. The preferred emulsifiers are cetyl phosphate (Amphisol® A), diethanolamine cetyl phosphate (Amphisol®), potassium cetyl phosphate (Amphisol® K), PVP Eicosene copolymer, acrylates/$C_{10-30}$-alkyl acrylate crosspolymer, PEG-20 sorbitan isostearate, sorbitan isostearate, and mixtures thereof. The one or more emulsifiers are present in a total amount about 0.01 wt. % to about 20 wt. % of the total weight of the composition of the present invention. Preferably, about 0.1 wt. % to about 10 wt. % of emulsifiers are used.

The lipid phase of the topical compositions can advantageously be chosen from mineral oils and mineral waxes; oils such as triglycerides of caprinic acid or caprylic acid, preferable castor oil; oils or waxes and other natural or synthetic oils, in an preferred embodiment esters of fatty acids with alcohols e.g. isopropanol, propylene glycol, glycerin or esters of fatty alcohols with carboxylic acids or fatty acids; alkylbenzoates; and/or silicone oils such as dimethylpolysiloxane, diethylpolysiloxane, diphenylpolysiloxane, cyclomethicones and mixtures thereof.

Exemplary fatty substances which can be incorporated in the oil phase of the emulsion, micro-emulsion, oleo gel, hydrodispersion or lipodispersion of the present invention are advantageously chosen from esters of saturated and/or unsaturated, linear or branched alkyl carboxylic acids with 3 to 30 carbon atoms, and saturated and/or unsaturated, linear and/or branched alcohols with 3 to 30 carbon atoms as well as esters of aromatic carboxylic acids and of saturated and/or unsaturated, linear or branched alcohols of 3-30 carbon atoms. Such esters can advantageously be selected from octylpalmitate, octylcocoate, octylisostearate, octyldodecylmyristate, cetearylisononanoate, isopropyl-myristate, isopropylpalmitate, isopropylstearate, isopropyloleate, n-butylstearate, n-hexyllaureate, n-decyloleat, isooctylstearate, isononylstearate, isononylisononanoate, 2-ethyl hexylpalmitate, 2-ethylhexyllaurate, 2-hexyldecylstearate, 2-octyldodecylpalmitate, stearylheptanoate, oleyloleate, oleylerucate, erucyloleate, erucylerucate, tridecylstearate, tridecyltrimellitate, as well as synthetic, half-synthetic or natural mixtures of such esters e.g. jojoba oil.

Other fatty components suitable for use in the topical compositions of the present invention include polar oils such as lecithins and fatty acid triglycerides, namely triglycerol esters of saturated and/or unsaturated, straight or branched carboxylic acid with 8 to 24 carbon atoms, preferably of 12 to 18 carbon-atoms whereas the fatty acid triglycerides are preferably chosen from synthetic, half synthetic or natural oils (e.g. cocoglyceride, olive oil, sun flower oil, soybean oil, peanut oil, rape seed oil, sweet almond oil, palm oil, coconut oil, castor oil, hydrogenated castor oil, wheat oil, grape seed oil, macadamia nut oil and others); apolar oils such as linear and/or branched hydrocarbons and waxes e.g. mineral oils, vaseline (petrolatum); paraffins, squalane and squalene, polyolefins, hydrogenated polyisobutenes and isohexadecanes, favored polyolefins are polydecenes; dialkyl ethers such as dicaprylylether; linear or cyclic silicone oils such as preferably cyclomethicone (octamethylcyclotetrasiloxane; cetyldimethicone, hexamethylcyclotri-siloxane, polydimethylsiloxane, poly(methylphenylsiloxane) and mixtures thereof.

Other fatty components which can advantageously be incorporated in topical compositions of the present invention are isoeikosane; neopentylglycoldiheptanoate; propyleneglycol-dicaprylate/dicaprate; caprylic/capric/diglycerylsuccinate; butyleneglycol caprylat/caprat; $C_{12-13}$-alkyllactate; di-$C_{12-13}$ alkyltartrate; triisostearin; dipentaerythrityl hexacaprylat-/hexacaprate; propylenglycolmonoisostearate; tricaprylin; dimethylisosorbid. Especially beneficial is the use of mixtures $C_{12-15}$-alkylbenzoate and 2-ethylhexylisostearate, mixtures $C_{12-15}$-alkylbenzoate and isotridecylisononanoate as well as mixtures of $C_{12-15}$-alkylbenzoate, 2-ethylhexylisostearate and isotridecylisononanoate.

The oily phase of the compositions of the present invention can also contain natural vegetable or animal waxes such as bee wax, china wax, bumblebee wax and other waxes of insects as well as shea butter and cocoa butter.

A moisturizing agent may be incorporated into a topical composition of the present invention to maintain hydration or rehydrate the skin. Moisturizers that prevent water from evaporating from the skin by providing a protective coating are called emollients. Additionally an emollient provides a softening or soothing effect on the skin surface and is generally considered safe for topical use. Preferred emollients include mineral oils, lanolin, petrolatum, capric/caprylic triglyceraldehydes, cholesterol, silicones such as dimethicone, cyclomethicone, almond oil, jojoba oil, avocado oil, castor oil, sesame oil, sunflower oil, coconut oil and grape seed oil, cocoa butter, olive oil aloe extracts, fatty acids such as oleic and stearic, fatty alcohols such as cetyl and hexadecyl (EN-JAY), diisopropyl adipate, hydroxybenzoate esters, benzoic acid esters of $C_{9-15}$-alcohols, isononyl iso-nonanoate, ethers such as polyoxypropylene butyl ethers and polyoxypropylene cetyl ethers, and $C_{12-15}$-alkyl benzoates, and mixtures thereof. The most preferred emollients are hydroxybenzoate esters, aloe vera, $C_{12-15}$-alkyl benzoates, and mixtures thereof. An emollient is present in an amount of about 1 wt. % to about 20 wt. % of the total weight of the composition. The preferred amount of emollient is about 2 wt. % to about 15 wt. %, and most preferably about 4 wt. % to about 10 wt. %.

Moisturizers that bind water, thereby retaining it on the skin surface are called humectants. Suitable humectants can be incorporated into a topical composition of the present invention such as glycerin, polypropylene glycol, 1,2-pentandiol, polyethylene glycol, lactic acid, pyrrolidone carboxylic acid, urea, phospholipids, collagen, elastin, ceramides, lecithin sorbitol, PEG-4, and mixtures thereof. Additional suitable moisturizers are polymeric moisturizers of the family of water soluble and/or swellable/and/or with water gelating polysaccharides such as hyaluronic acid, chitosan and/or a fucose rich polysaccharide which is e.g. available as Fucogel®1000 (CAS-Nr. 178463-23-5) by SOLABIA S. One or more humectants are optionally present at about 0.5 wt. % to about 8 wt. % in a composition of the present invention, preferably about 1 wt. % to about 5 wt. %.

The aqueous phase of the preferred topical compositions of the present invention can contain the usual cosmetic or pharmaceutical additives such as alcohols, especially lower alcohols, preferably ethanol and/or isopropanol, low diols or polyols and their ethers, preferably propyleneglycol, glycerin, ethyleneglycol, ethyleneglycol monoethyl- or monobutylether, propyleneglycol monomethyl- or -monoethyl- or -monobutylether, diethyleneglycol monomethyl- or -monoethylether and analogue products, polymers, foam stabilizers; electrolytes and especially one or more thickeners. Thickeners that may be used in compositions of the present invention to assist in making the consistency of a product suitable include carbomer, siliciumdioxide, magnesium and/or aluminum silicates, beeswax, stearic acid, stearyl alcohol polysaccharides and their derivatives such as xanthan gum, hydroxypropyl cellulose, polyacrylamides, acrylate crosspolymers preferably a carbomer, such as Carbopole® of type 980, 981, 1382, 2984, 5984 alone or mixtures thereof. Suitable neutralizing agents which may be included in the composition of the present invention to neutralize components such as e.g. an emulsifier or a foam builder/stabilizer include but are not limited to alkali hydroxides such as a sodium and potassium hydroxide; organic bases such as diethanolamine (DEA), triethanolamine (TEA), aminomethyl propanol, and mixtures thereof; amino acids such as arginin and lysine and any combination of any foregoing. The neutralizing agent can be present in an amount of about 0.01 wt. % to about 8 wt. % in the composition of the present invention, preferably, 1 wt. % to about 5 wt. %.

The addition of electrolytes into the composition of the present invention may be necessary to change the behavior of a hydrophobic emulsifier. Thus, the emulsions/microemulsions of this invention may contain preferably electrolytes of one or several salts including anions such as chloride, sulfates, carbonate, borate and aluminate, without being limited thereto. Other suitable electrolytes can be on the basis of organic anions such as, but not limited to, lactate, acetate, benzoate, propionate, tartrate and citrate. As cations preferably ammonium, alkylammonium, alkali- or alkaline earth metals, magnesium-, iron- or zinc-ions are selected. Especially preferred salts are potassium and sodium chloride, magnesium sulfate, zinc sulfate and mixtures thereof. Electrolytes can be present in an amount of about 0.01 wt. % to about 8 wt. % in the composition of the present invention.

The topical compositions of the invention can preferably be provided in the form of a lotion, a thickened lotion, a gel, a cream, a milk, an ointment, a powder or a solid tube stick and can be optionally be packaged as an aerosol and can be provided in the form of a mousse, foam or a spray. The compositions according to the invention can also be in the form of a suspension or dispersion in solvents or fatty substances, or alternatively in the form of an emulsion or microemulsion (in particular of O/W or W/O type, O/W/O or W/O/W-type), such as a cream or a milk, a vesicular dispersion, in the form of an ointment, a gel, a solid tube stick or an aerosol mousse. The emulsions can also contain anionic, nonionic, cationic or amphoteric surfactants.

The topical application is preferably applied at least once per day, e.g. two or three times a day. Usually it takes at least two days until the desired effect is achieved. However, it can take several weeks or even months until the desired effect is achieved.

According to the invention for preparing the compositions the active ingredients can be used as such or in an encapsulated form, for example in a liposomal form. Liposomes are preferably formed with lecithins with or without addition of sterols or phytosterols. The encapsulation of the active ingredients can be alone or together with other active ingredients.

In the composition of the invention, in particular the topical compositions of the invention, the compound of formula (I) is contained in an amount of preferably 0.0001 wt.-% to about 50 wt.-%, based on the total weight of the composition. More preferably, the compound is contained in the composition in an amount of about 0.01 wt.-% to about 20 wt.-%, more preferably in an amount of about 0.1 wt.-% to about 5 wt.-%, in particular in an amount of about 0.2 wt—% to 1 wt.-%, based on the total amount of the composition.

In case that the (preferably topical) composition of the invention contains a further active ingredient, this further active ingredient is contained in an amount of preferably 0.0001 wt.-% to about 50 wt.-%, based on the total weight of the composition. More preferably, the further active ingredient is contained in the composition in an amount of about 0.01 wt.-% to about 20 wt.-%, more preferably in an amount of about 0.01 wt.-% to about 1 wt.-%, in particular in an amount of about 0.1 wt.-% to 1 wt. %, based on the total amount of the composition.

Regarding the kind of the topical composition and the preparation of the topical compositions as well as for further suitable additives, it can be referred to the pertinent literature, e.g. to Novak G. A., Die kosmetischen Präparate—Band 2, Die kosmetischen Präparate—Rezeptur, Rohstoffe, wissenschaftliche Grundlagen (Verlag für Chem. Industrie H. Ziolkowski KG, Augsburg).

It is furthermore possible to provide the compositions of the present invention as oral composition, e.g. in the form of pills, tablets, capsules which may contain granules or pellets, as a liquid, oral composition or as an additive to foodstuff as is generally known to a skilled person. Useful procedures and useful additives for preparing the oral compositions of the present invention are e.g. disclosed in the standard literature Remington: The Science and Practice of Pharmacy, Lippincot, Williams & Wilking (Editors) 2000, which is included herein by reference.

As usual additives for oral compositions, in particular for tablets, usual excipients such as micro-crystalline cellulose, sodium citrate, calcium carbonate, disodium or dipotassium phosphate, sodium or potassium phosphate, glycine, disintegration agents such as starch or alginic acid, binders such as polyvinylpyrolidone, saccharose, gelatin and gum arabicum lubricants such as magnesium stearate, sodium lauryl sulfate or talcum can be used. If the compositions are filed into gelatin capsules, usual additives for the preparation of granules are lactose or lactate as well as polyethylene glycols with a high molecular weight. Further additives and excipients as well as additives and excipients for other oral compositions and for food additives are known to a skilled person, and it can be referred to the pertinent literature such as "Grundzüge der Lebensmitteltechnik", Horst Dieter Tscheuschner (Editor), 2. Edition, Hamburg, Beers 1996.

The total content of the active ingredients in the oral compositions of the present invention is usually about 1% to 90%, preferably about 10% to 80%, e.g. about 50% or more. The application is such that the desired effect occurs and depends on the patient and the desired effect. A usual daily dosage can be in a range from about 0.1 µg/day to 50 mg/day, e.g. about 20 µg/day to 2 mg/day.

The ability of the compounds and compositions of the present invention to reduce skin wrinkles can be assessed by profilometric methods described in "Skin topography measurement by interference fringe projection: a technical validation". (Lagarde J M; Rouvrais C; Black D; Diridollou S; Gall Y, Skin research and technology: official journal of International Society for Bioengineering and the Skin (ISBS) [and] International Society for Digital Imaging of Skin (IS-DIS) [and] International Society for Skin Imaging (ISSI) (2001 May), 7(2), 112-21 or "Direct and non-direct measurement techniques for analysis of skin surface topography". Fischer T W; Wigger-Alberti W; Elsner P., Skin pharmacology and applied skin physiology (1999 January-April), 12(1-2), 1-11.

The ability of the compounds and compositions of the present invention to stimulate or protect hair growth can be determined with a mouse model described for example in WO 9817273. Instead of using Cyclophosphamide (Neostar, Pharmacia) to damage hair follicle Mitomycin, or Methotrexate can be used. It is also possible to detect hair growth acceleration with newborn mice. They have a synchronized hair cycle and approximately after 3 weeks all hair follicles go into the telogen phase. Then the animals are treated and it is evaluated how fast and to what extend the hair is growing Similar tests using in vitro or in vivo setups can also be found in J. Invest. Dermato. symposium proceedings 3rd Int. Meeting of Hair Research Societies, 8/1, p. 39-45 (2003).

It also is possible to perform a clinical study including males suffering from alopecia using the TrichoScan analysis tool described in R. Hoffmann, J. Invest. Dermato. symposium proceedings 3rd Int. Meeting of Hair Research Societies, 8/1, p. 109-115 (2003).

The compositions of the present invention can also be in the form of injectable compositions, in particular if the compositions are for promoting hair growth. The preparation of injectable compositions is known to a skilled person, and it can be referred to the pertinent literature, in particular to Remington already cited above.

The compounds of formula (I) can also be present as hydrates or solvates, and the hydrates and solvates of the active ingredients are also encompassed by the present invention.

The following examples exemplify the invention, but they should not be construed as limiting the invention.

EXAMPLE 1

Synthesis of 4-Phenyl-Butyric Acid 3-(2,4-Dihydroxy-3,3-Dimethyl-Butyrylamino)-Propyl Ester

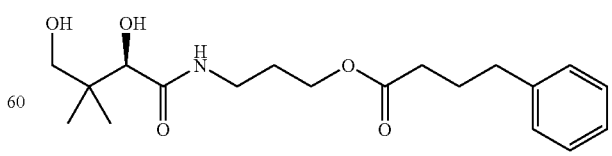

To a solution of D-Panthenol (20.5 g, 100.0 mmol, 1.0 eq.) in dry acetone (400 mL) were added sodium sulphate anhydrous (50.0 g) and p-TsOH monohydrate (1.0 g, 4.0 mmol, 0.04 eq.). The reaction mixture was stirred at room temperature overnight. p-TsOH monohydrate (500 mg, 2.63 mmol, 0.03 eq.) was added again and the reaction mixture stirred at room temperature for 6 days until the reaction showed nearly no starting material and no further conversion anymore. Most of the acetone was removed under low pressure and the residue was suspended in a saturated aqueous solution of NaHCO$_3$ (150 mL) and extracted five times with ethyl acetate (200 mL). The organic layers were combined and washed with brine (100 mL) once. The organic layer was dried over Na$_2$SO$_4$, filtered and the solvent was removed under low pressure. The colourless and oily residue was dried under high-vacuum at room temperature to yield 22.7 g (93%) of the product as a white solid. $^1$H NMR (CDCl$_3$) δ=1.01 (s 3H), 1.05 (s, 3H), 1.44 (s, 3H), 1.47 (s, 3H), 1.70-1.73 (m, 2H), 3.27-3.71 (m, 9H), 4.11 (s, 1H), 6.85 (s, 1H). $^{13}$C NMR (CDCl$_3$) δ=18.7, 18.9, 22.1, 29.4, 32.4, 33.0, 35.3, 59.1, 71.5, 76.6, 99.1, 171.0.

Panthenolacetonide (15.0 g, 61.2 mmol, 1.0 eq.) was dissolved in DCM (250 mL) and cooled to 0° C. with an ice bath. Pyridine (12.1 g, 153 mmol, 2.5 eq.) was first added and then 4-Phenylbutanoylchloride (11.7 g, 64.2 mmol, 1.05 eq.) in DCM (70 mL). The reaction was exothermic, therefore the temperature was held in a range of –5° C. to 5° C. The ice-bath was removed after complete addition and the reaction mixture was allowed to warm up to room temperature overnight. The reaction was quenched with a saturated aqueous solution of Na$_2$CO$_3$ (150 mL) and ethyl acetate (200 mL) was added. The layers were separated and the aqueous layer was extracted twice with of ethyl acetate (150 mL). The combined organic layers were washed once with a saturated aqueous solution of Na$_2$CO$_3$ (150 mL) and once with brine (150 mL). The organic layer was dried over Na$_2$SO$_4$, the solvent was removed under low pressure and the residue dried under high vacuum at room temperature. 24.95 g (104.2%) of a pale yellow oil were obtained. The crude product was purified by flash chromatography over silica gel with a mixture of tBME/DIPE (1:2, +0.5% triethylamine). 24.1 g (100%) of the acylated Panthenolacetonide as a colourless oil were obtained. $^1$H NMR (CDCl$_3$) δ=0.99 (s, 3H), 1.05 (s, 3H), 1.41 (s, 3H), 1.46 (s, 3H), 1.82-1.86 (m, 2H), 1.92-2.00 (m, 2H), 2.30-2.35 (q, 2H), 2.61-2.67 (t, 2H), 3.19-3.43 (m, 3H), 3.65-3.69 (d, 1H), 4.08-4.15 (m, 3H), 6.71-6.74 (t, 1H), 7.15-7.19 (m, 3H), 7.24-7.31 (m, 2H). $^{13}$C NMR (CDCl$_3$) δ=18.7, 18.9, 22.1, 22.9, 26.4, 27.0, 28.8, 29.5, 32.7, 32.9, 33.2, 33.5, 35.1, 35.6, 49.4, 61.9, 68.2, 71.4, 76.8, 99.0, 126.0, 128.3, 128.4, 141.2, 169.7, 173.3. DC (silica gel/tBME/DIPE (1:2, +0.5% triethylamine)) R$_f$=0.41 and 0.25.

The acylated Panthenolacetonide (24.1 g, 61.2 mmol, 1.0 eq.) was suspended in a mixture of methanol (150 mL) and water (100 mL, deionised). p-TsOH monohydrate (500 mg, 2.63 mmol, 0.04 eq.) was added and the reaction mixture was stirred overnight at room temperature. The reaction mixture was quenched with a saturated aqueous solution of NaHCO$_3$ (40 mL) and the methanol was distilled of under reduced pressure. The residue, a white suspension, was extracted five times with ethyl acetate (200 mL). The organic layers were combined and washed once with a saturated aqueous solution of NaHCO$_3$ (100 mL) and once with brine (150 mL). The organic layer was dried over Na$_2$SO$_4$, filtered and the solvent was removed under reduced pressure. The oily residue was dried under high vacuum at room temperature overnight. 21.3 g (99%) of pale yellow oil were obtained. The crude product was purified by flash chromatography over silica gel with tBME as solvent. 14.9 g (69%) of 4-phenyl-butyric acid 3-(2, 4-dihydroxy-3,3-dimethyl-butyrylamino)-propyl ester as a colourless oil were obtained. $^1$H NMR (CDCb$_3$) δ=0.90 (s, 3H), 0.98 (s, 3H), 1.79-1.99 (m, 4H), 2.3-2.36 (t, 2H), 2.61-2.66 (t, 2H), 3.23-3.42 (m, 2H), 3.47 (s, 2H), 3.99-4.00 (d, 1H), 4.07-4.13 (m, 3H), 4.64-4.65 (d, 1H), 7.15-7.30 (m, 5H). $^{13}$C NMR (CDCl$_3$) δ=20.3, 21.2, 26.4, 28.7, 33.5, 35.1, 39.3, 60.5, 62.0 71.2 76.7 77.1-77.6 (CDCl$_3$), 126.0, 128.4, 128.5, 141.3, 141.6, 173.7, 173.7. MS (ESI) m/z=352.2 (100) [M+H$^+$], 374.2 (5) [M+Na$^+$], 188 (5) [M-(4-Phenylbutyric acid)+H+], DC (silica gel/tBME) R$_f$=0.25.

EXAMPLE 2

Synthesis of 4-Phenyl-Butyric Acid 2-[(Pyridine-3-Carbonyl)Amino]-Ethyl Ester

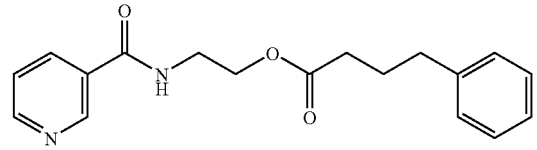

Ethyl nicotinate (15.1 g, 100.0 mmol, 1.0 eq.) and Ethanolamine (6.1 g, 100.0 mmol, 1.0 eq.) were dissolved in toluene (80 mL). The reaction mixture was heated to 80° C. and stirred for 48 h. During the reaction the mixture changed into a sticky emulsion. The emulsion was cooled down to room temperature and the lower phase became solid. The upper liquid phase was decanted and the orange solid was crystallised twice, first from ethyl acetate and then from acetone. The crystals were dried under high vacuum at room temperature to give 7.1 g (42%) of the product as a white, free flowing powder. The $^1$H NMR and the 13C NMR corresponds to the literature (Ogawa, T.; Hatayama, K.; Maeda, H.; Kita, Y. Chem. Pharm. Bull. 1994, 42 (8) 1579-1589). $^1$H NMR (CDCl3) δ=3.60-3.64 (q, 2H), 3.82-3.85 (t, 2H), 4.00 (s, 1H), 7.33-7.39 (m, 2H), 8.10-8.14 (m, 1H), 8.64-8.67 (q, 1H), 8.99-9.00 (t, 1H). $^{13}$C NMR (CDCl3) δ=42.8, 61.5, 123.6, 130.2, 135.5, 147.8, 152.0, 166.4.

N-(2-Hydroxy-ethyl)-nicotinamide (3.3 g, 20.0 mmol, 1.0 eq.) was dissolved in DCM (100 mL) and pyridine (20 mL). The light yellow solution was cooled to 2° C. A solution of 4-phenylbutanoylchloride (3.65 g of 20 mmol, 1.0 eq.) in DCM (25 mL) was slowly added. The reaction mixture was stirred for 1 h at 0° C. The reaction mixture was evaporated under reduced pressure and the residue was dissolved in water (100 mL) and ethyl acetate (100 mL). The layers were separated and the aqueous phase was extracted with ethyl acetate (75 mL). The combined organic layers were washed with a saturated aqueous solution of NaHCO$_3$ (50 mL) and of brine (50 mL). The organic layer was dried over Na$_2$SO$_4$, filtrated and evaporated under reduced pressure. The yellow, oily residue was dried at high vacuum at room temperature to give 6.2 g (100%) of the product as yellow oil. The crude product was purified by flash chromatography over silica gel with ethyl acetate to yield the pure 4-phenyl-butyric acid 2-[(pyridine-3-carbonyl)amino]-ethyl ester 5.6 g (89%) as a light yellow oil. $^1$H NMR (CDCl3) δ=1.87-1.95 (m, 2H), 2.29-2.34 (m, 2H), 2.58-2.63 (m, 2H), 3.67-3.72 (m, 2H), 4.25-4.29 (m, 2H), 7.11-7.41 (m, 7H), 8.08-8.12 (m, 1H), 8.65-8.67 (q, 1H), 8.99-9.00 (d, 1H). $^{13}$C NMR (CDCl3) δ=26.3, 33.4, 35.0, 39.6, 62.9, 123.5, 126.0, 128.4, 128.8, 130.0, 135.2, 141.1, 148.1, 152.1, 165.8, 173.9. MS (ESI) m/z=313.2 (100) [M+H+]. DC (silica gel/ethyl acetate): R$_F$=0.32.

EXAMPLE 3

Synthesis of 4-Phenyl-butyric acid 1,5-dimethyl-1-(4-methyl-cyclohex-3-enyl)-hex-4-enyl ester

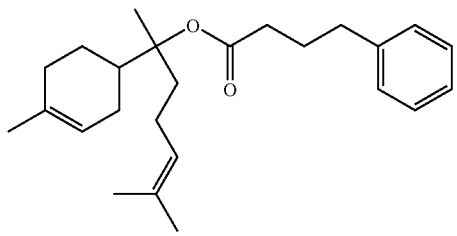

To a solution of rac-alpha-Bisabolol (267 mg, 1.2 mmol, 1.2 eq.) in toluene (5 mL), silver cyanide (268 mg, 2 mmol, 2.0 eq.) was added. The reaction mixture was heated to 80° C. Then 4-phenylbutanoylchloride (182 mg, 1 mmol, 1.0 eq.) was added and the reaction mixture was stirred overnight at 80° C. A sample was taken and analyzed by GC-MS. The mass of the alpha-Bisabolol was found: (EI) m/z=204, 147, 119, 109, 104, 91, 69, 41. The reaction mixture containing 4-phenyl-butyric acid 1,5-dimethyl-1-(4-methyl-cyclohex-3-enyl)-hex-4-enyl ester can be worked up by standard procedures.

EXAMPLE 4

Synthesis of N-furan-2-yl-methyl-4-phenyl-N-(9H-purin-6-yl)-butyramide

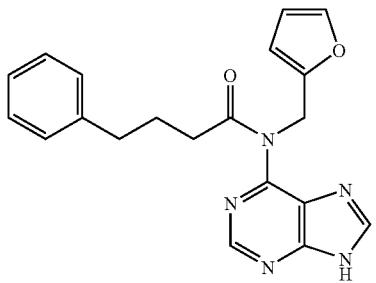

To a suspension of Kinetin (1.26 g, 5.85 mmol, 1.0 eq.) in dry DMF (25 mL) was added triethylamine (651 mg, 6.44 mmol, 1.1 eq.). Then trityl bromide (2.08 g, 6.44 mmol, 1.1 eq.) was added and the mixture was stirred at room temperature over night. Reaction control by DC (hexane/ethyl acetate 1:1) showed still Kinetin. The reaction mixture was stirred further 3 hours at 50° C. Reaction control by DC (hexane/ethyl acetate 1:1) showed only small traces of remaining Kinetin. The reaction mixture was quenched with a saturated aqueous solution of $NaHCO_3$ (30 mL). The yellow solution was extracted three times with ethyl acetate (75 mL). The combined organic layers were washed with a saturated aqueous solution of $NaHCO_3$ (50 mL) and once with brine (50 mL). The organic layer was dried over $Na_2SO_4$, filtered and the solvent was removed under reduced pressure. The residue was dried in high-vacuum at room temperature to yield 3.21 g (120%) of a brown amorphous solid. The crude product was purified by flash-chromatography with ethyl acetate/hexane 1:2 as eluent. 1.41 g (53%) of a light beige solid were obtained. —$^1$H NMR ($CDCl_3$) δ=4.82-4.83 (d, 2H), 6.29 (s, 2H), 6.45-6.49 (t, 1H), 7.14-7.31 (m, 16H), 7.71 (s, 1H), 8.14 (s, 1H). —$^{13}$C NMR ($CDCl_3$) δ=75.8, 107.5, 110.4, 121.3, 127.9, 128.0, 129.8, 141.4, 142.2, 151.8, 152.4, 154.6. —DC (ethyl acetate/hexane 1:2): $R_f$=0.33.

A suspension of furane-2-ylmethyl-(9-trityl-9H-purine-6-yl)-amine (1.00 g, 2.186 mmol, 1.0 eq.) in toluene (40 mL) was heated to 65° C. and a clear pale yellow solution was obtained. Then silver cyanide (585 mg, 4.371 mmol, 2.0 eq.), triethylamine (266 mg, 2.633 mmol, 1.2 eq.) and 4-phenylbutanoyl chloride (439 mg, 2.404 mmol, 1.1 eq.) were added. The reaction mixture was stirred for 3 hours at 65° C. Reaction control by DC showed still starting material. Another portion of triethylamine (266 mg, 2.633 mmol, 1.2 eq.) and 4-phenylbutanoyl chloride (439 mg, 2.404 mmol, 1.1 eq.) were added. The reaction mixture was stirred for 1 hour at 70° C. Reaction control by DC showed no more starting material. The reaction mixture was cooled to room temperature, ethyl acetate (100 mL) was added and the solution was washed with a saturated aqueous solution of $NaHCO_3$ (50 mL) and brine (50 mL). The organic layer was dried over $Na_2SO_4$, the solvent was removed under reduced pressure and the residue was dried in high vacuum at room temperature to yield 1.93 g (146%) of a brown oil. The crude product was purified by flash-chromatography with a mixture of hexane/ethyl acetate 4:1 to give 720 mg (55%) of a pale yellow solid. —$^1$H NMR ($CDCl_3$) δ=1.95-2.05 (m, 2H), 2.56-2.63 (m, 4H), 5.50 (s, 2H), 6.14-6.19 (m, 2H), 7.06-7.42 (m, 21H), 8.00 (s, 1H), 8.41 (s, 1H). —$^{13}$C NMR ($CDCl_3$) δ=26.9, 35.1, 35.2, 43.6, 76.4, 108.0, 110.2, 125.7, 128.1, 128.2, 128.5, 129.7, 140.9, 141.8, 145.0, 151.3, 153.1, 154.4, 173.8. —DC (hexane/ethyl acetate 4:1): $R_f$=0.40.

N-furane-2-ylmethyl-4-phenyl-N-(9-trityl-9H-purine-6-yl)-butyramide (650 mg, 1.11 mmol) was dissolved in a mixture of DCM with 1% deionised water and 0.2% TFA (55 mL). The clear pale brown solution was stirred for 2 hours at room temperature. Reaction control by DC showed no more starting material. To the reaction mixture was added ethyl acetate (100 mL) and the solution was washed twice with a saturated aqueous solution of $NaHCO_3$ solution (50 mL). The combined aqueous layers were extracted twice with ethyl acetate (50 mL). The combined organic layers were washed once with brine (75 mL) and dried over $Na_2SO_4$. The solvent was removed under reduced pressure and the residue was dried in high vacuum at room temperature to yield 700 mg (175%) of a pale brown solid. The crude product was purified by flash-chromatography using hexane/ethyl acetate 1:1 to give 260 mg (65%) of N-furan-2-yl-methyl-4-phenyl-N-(9H-purin-6-yl)-butyramide as a colourless gum. —$^1$H NMR (MeOH-$d_4$) δ=1.76-1.86 (m, 2H), 2.37-2.45 (m, 4H), 4.78 (s, 2H), 5.23 (s, 2H), 6.00-6.06 (t, 1H), 6.06-6.07 (t, 1H), 6.89-7.05 (m, 4H), 7.11-7.12 (d, 1H), 8.31 (s, 1H), 8.63 (s, 1H). —$^{13}$C NMR (MeOH-$d_4$) δ=28.2, 35.5, 35.9, 44.5, 109.4, 111.2, 126.9, 129.3, 129.4, 142.7, 143.4, 146.2, 152.0, 153.0, 175.5. —DC (hexane/ethyl acetate 1:1): $R_f$=0.20.

EXAMPLE 5

| Anti-aging cream O/W emulsion with 4-Phenyl-Butyric Acid 3-(2,4-Dihydroxy-3,3-Dimethyl-Butyrylamino)-Propyl Ester (Compound of Example 1) | |
|---|---|
| Ingredients | % (w/w) |
| Glyceryl Myristate | 4.00 |
| Cetyl Alcohol | 2.00 |
| Steareth-2 | 2.00 |
| Steareth-21 | 2.00 |
| Isopropyl Myristate | 5.00 |

-continued

Anti-aging cream
O/W emulsion with 4-Phenyl-Butyric Acid
3-(2,4-Dihydroxy-3,3-Dimethyl-Butyrylamino)-
Propyl Ester (Compound of Example 1)

| Ingredients | % (w/w) |
|---|---|
| Caprylic/Capric Triglyceride | 8.00 |
| BHT | 0.05 |
| Dimethicone | 2.00 |
| Phenoxyethanol & Methylparaben & Ethylparaben & Butylparaben & Propylparaben & Isobutylparaben | 0.80 |
| Compound of Example 1 | 0.50 |
| Water | Ad 100 |
| Xanthan Gum | 0.50 |
| Disodium EDETA | 0.10 |
| Propylene Glycol | 4.00 |

EXAMPLE 6

Anti-aging cream
O/W emulsion with 4-Phenyl-Butyric Acid
2-[(Pyridine-3-Carbonyl)Amino]-Ethyl
Ester (Compound of Example 2

| Ingredients | % (w/w) |
|---|---|
| Glyceryl Myristate | 4.00 |
| Cetyl Alcohol | 2.00 |
| Steareth-2 | 2.00 |
| Steareth-21 | 2.00 |
| Isopropyl Myristate | 5.00 |
| Caprylic/Capric Triglyceride | 8.00 |
| BHT | 0.05 |
| Dimethicone | 2.00 |
| Phenoxyethanol & Methylparaben & Ethylparaben & Butylparaben & Propylparaben & Isobutylparaben | 0.80 |
| Compound of example 2 | 0.50 |
| Water | Ad 100 |
| Xanthan Gum | 0.50 |
| Disodium EDETA | 0.10 |
| Propylene Glycol | 4.00 |

EXAMPLE 7

Anti-aging cream
O/W emulsion with 4-Phenyl-butyric acid
1,5-dimethyl-1-(4-methyl-cyclohex-3-enyl)-
hex-4-enyl ester (Compound of Example 3)

| Ingredients | % (w/w) |
|---|---|
| Glyceryl Myristate | 4.00 |
| Cetyl Alcohol | 2.00 |
| Steareth-2 | 2.00 |
| Steareth-21 | 2.00 |
| Isopropyl Myristate | 5.00 |
| Caprylic/Capric Triglyceride | 8.00 |
| BHT | 0.05 |
| Dimethicone | 2.00 |
| Phenoxyethanol & Methylparaben & Ethylparaben & Butylparaben & Propylparaben & Isobutylparaben | 0.80 |
| Compound of example 3 | 0.50 |
| Water | Ad 100 |
| Xanthan Gum | 0.50 |
| Disodium EDETA | 0.10 |
| Propylene Glycol | 4.00 |

What is claimed is:

1. A compound which is 4-phenylbutyric acid 2-[(pyridine-3-carbonyl)amino]-ethyl ester.

2. A topical composition comprising 4-phenylbutyric acid 2-[(pyridine-3-carbonyl)amino]-ethyl ester and a cosmetically or pharmaceutically acceptable excipient or diluent.

3. The composition as in claim 2 wherein 4-phenylbutyric acid 2-[(pyridine-3-carbonyl)amino]-ethyl ester is present in a concentration of 0.001 to 50 wt.-%, based on the total weight of the composition.

4. The composition as in claim 2 wherein 4-phenylbutyric acid 2-[(pyridine-3-carbonyl)amino]-ethyl ester is present in a concentration of 0.01 to 1 wt.-%, based on the total weight of the composition.

* * * * *